US008669115B2

(12) United States Patent
Pagoria et al.

(10) Patent No.: US 8,669,115 B2
(45) Date of Patent: Mar. 11, 2014

(54) SPOT TEST KIT FOR EXPLOSIVES DETECTION

(75) Inventors: Philip F. Pagoria, Livermore, CA (US); Richard E. Whipple, Livermore, CA (US); Peter J. Nunes, Danville, CA (US); Joel Del Eckels, Livermore, CA (US); John G. Reynolds, San Ramon, CA (US); Robin R. Miles, Danville, CA (US); Marina L. Chiarappa-Zucca, Livermore, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 523 days.

(21) Appl. No.: 12/785,299

(22) Filed: May 21, 2010

(65) Prior Publication Data

US 2010/0229633 A1    Sep. 16, 2010

Related U.S. Application Data

(62) Division of application No. 11/159,451, filed on Jun. 22, 2005, now abandoned.

(60) Provisional application No. 60/583,161, filed on Jun. 24, 2004.

(51) Int. Cl.
*G01N 21/00*        (2006.01)

(52) U.S. Cl.
USPC ........ 436/164; 436/518; 436/169; 435/283.1; 435/287.1; 435/288.7

(58) Field of Classification Search
USPC ............ 436/518, 164, 169; 435/283.1, 287.1, 435/288.7
See application file for complete search history.

(56) References Cited

U.S. PATENT DOCUMENTS

| 5,480,612 | A | * | 1/1996 | Margalit | 422/430 |
| 5,638,166 | A |   | 6/1997 | Funsten et al. | |
| 5,679,584 | A |   | 10/1997 | Mileaf et al. | |
| 5,770,458 | A | * | 6/1998 | Klimov et al. | 436/518 |
| 6,470,730 | B1 |   | 10/2002 | Chamberlain | |
| 2003/0104506 | A1 | * | 6/2003 | Durst et al. | 435/7.92 |

(Continued)

FOREIGN PATENT DOCUMENTS

WO    WO 97/37212    10/1997

OTHER PUBLICATIONS

No author, Military M-256A1 Chemical Agent Detection and Identification Kit, Two Tigers Online, http://www.twotigersonline.com/m256.html, Apr. 25, 2005, 4 pages.

*Primary Examiner* — Melanie Y Brown
(74) *Attorney, Agent, or Firm* — Eddie E. Scott

(57) ABSTRACT

An explosion tester system comprising a body, a lateral flow membrane swab unit adapted to be removeably connected to the body, a first explosives detecting reagent, a first reagent holder and dispenser operatively connected to the body, the first reagent holder and dispenser containing the first explosives detecting reagent and positioned to deliver the first explosives detecting reagent to the lateral flow membrane swab unit when the lateral flow membrane swab unit is connected to the body, a second explosives detecting reagent, and a second reagent holder and dispenser operatively connected to the body, the second reagent holder and dispenser containing the second explosives detecting reagent and positioned to deliver the second explosives detecting reagent to the lateral flow membrane swab unit when the lateral flow membrane swab unit is connected to the body.

1 Claim, 3 Drawing Sheets

(56) References Cited

U.S. PATENT DOCUMENTS

| | | |
|---|---|---|
| 2004/0042934 A1 | 3/2004 | Nunes et al. |
| 2004/0265169 A1 | 12/2004 | Haas et al. |
| 2005/0064601 A1 | 3/2005 | Haas |
| 2005/0101027 A1 | 5/2005 | Haas |
| 2007/0141717 A1* | 6/2007 | Carpenter et al. ............ 436/172 |

* cited by examiner

SPOT TEST KIT FOR EXPLOSIVES DETECTION

CROSS-REFERENCE TO RELATED APPLICATIONS

This application is a Divisional of application Ser. No. 11/159,451 filed Jun. 22, 2005 now abandoned, entitled "Spot Test Kit for Explosives Detection". This application claims the benefit of U.S. Provisional Patent Application No. 60/583,161, filed Jun. 24, 2004, and titled "Spot Test Kit for Explosives Detection", which are incorporated herein by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to explosives and more particularly to testing for the presence of explosives.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information, "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See Fetterolf et al., Portable Instrumentation: New Weapons in the War Against Drugs and Terrorism," Proc. SPIE 2092 (1993) 40, Yinon and Zitrin, in Modern Methods and Applications in Analysis of Explosions, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a .gamma.-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

U.S. Pat. No. 5,679,584 for a method for chemical detection issued Oct. 2, 1997 to Daryl Sunny Mileaf and Noe Esau Rodriquez, II provides the following state of the art information, "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information, " . . . method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The preset invention provides an inspection tester system for testing a suspect surface for explosives. The system includes the step of providing a lateral flow membrane swab unit; providing a first explosives detecting reagent; providing a second explosives detecting reagent; swiping the suspect surface with the lateral flow membrane swab unit, delivering the first explosives detecting reagent to the lateral flow membrane swab unit, wherein if the lateral flow membrane swab unit becomes colored the test is positive for explosives and if no color appears the test for explosives is negative to this point; and delivering the second explosives detecting reagent to the lateral flow membrane swab unit, wherein if the lateral flow membrane swab unit becomes colored the test is positive for explosives and if no color appears the test for explosives is negative.

The inspection tester system comprises a body, a lateral flow membrane swab unit adapted to be removable connected to the body, a first explosives detecting reagent, a first reagent holder and dispenser operatively connected to the body, the first reagent holder and dispenser containing the first explosives detecting reagent and positioned to deliver the first explosives detecting reagent to the lateral flow membrane swab unit when the lateral flow membrane swab unit is connected to the body, a second explosives detecting reagent, and a second reagent holder and dispenser operatively connected to the body, the second reagent holder and dispenser containing the second explosives detecting reagent and positioned to deliver the second explosives detecting reagent to the lateral flow membrane swab unit when the lateral flow membrane swab unit is connected to the body.

The inspection tester of the present invention provides a simple, chemical, field spot-test to provide a rapid screen for the presence of a broad range of explosive residues. The inspection tester is fast, extremely sensitive, low-cost, very easy to implement, and provides a very low rate of false positives. The inspection tester for explosives provides a fast, sensitive, low-cost, very easy to implement system for testing the suspected packages. The inspection tester for explosives is inexpensive and disposable. The inspection tester for explosives has detection limits between 0.1 to 100 nanograms, depending on the type of explosives present. A large number of common military and industrial explosives can be easily detected such as HMX, RDX, NG, TATB, Tetryl, PSTN, TNT, DNT, TNB, DNB and NC. The inspection tester is small enough that a number of them can fit in a pocket or brief case.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
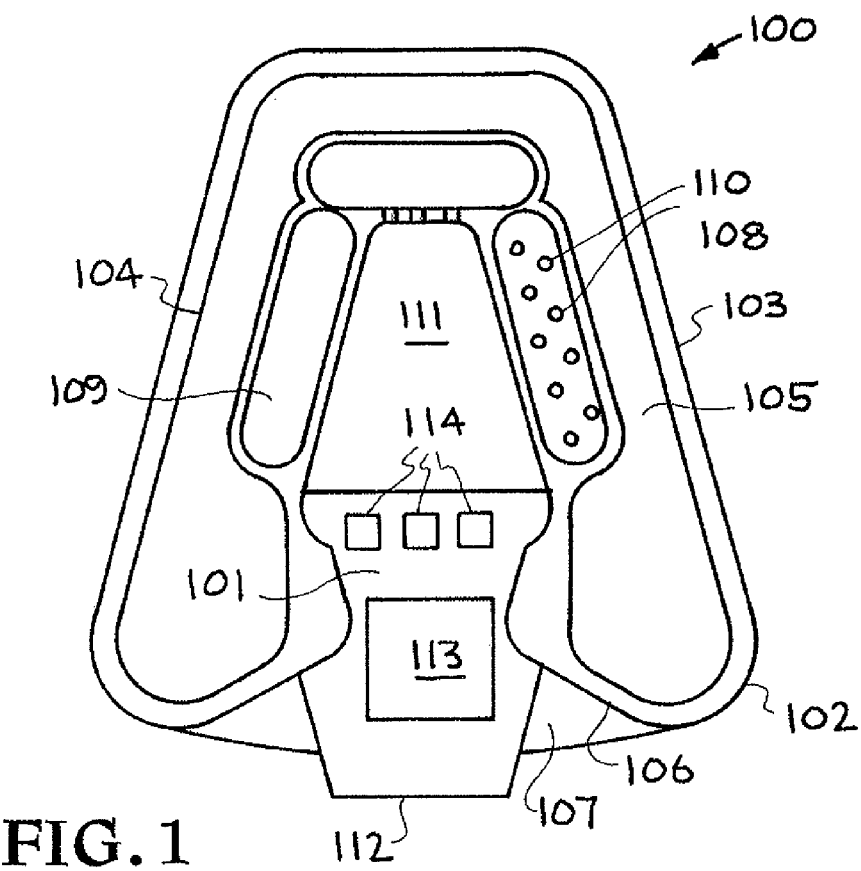
FIG. 1 illustrates an embodiment of the invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The ability to identify unknown explosives in the field is of utmost importance to the military, law enforcement and Homeland security forces worldwide. There have been many reports of the use of spot tests for the identification of explosives, some of which are listed below. They have been used in combination with thin-layer chromatography and in forensic analysis. There are some commercial companies (Mistral, Securesearch, Duram products) who have produced explosives identification kits similar to the one Applicants propose. They have incorporated similar color reagents and have been used by the military and law-enforcement agencies. Ex-spray and Duram products are probably the best commercial test kits produced thus far. They allow the identification of nitroaromatics, nitramines, ammonium nitrate, and recently the potassium chlorate-based explosives. Their systems are available as spray kits or solution-drop kits. The Duram product will also identify the peroxide explosives. Another company produced a swab kit that incorporates either diphenylamine or Wurster's salt that turns blue when it comes in contact with nitramines, oxidizers and nitrate esters. It is easy to use but is non-specific and would give a significant number of false positives.

Referring now to FIG. 1 of the drawings, an embodiment of an inspection tester for explosives constructed in accordance with the present invention is illustrated. This embodiment of the present invention is designated generally by the reference numeral 100. The inspection tester 100 is an all-inclusive, inexpensive, and disposable device. The inspection tester can be used anywhere as a primary screening tool by non-technical personnel to determine whether a surface contains explosives. The inspection tester 100 was developed to allow identification of explosives. This inspection tester may be used by first responders, military, law enforcement and Homeland Security.

The inspection tester 100 provides a small, disposable, one use system. The inspection tester 100 uses a simple and rapid method of operation. A removable swab unit sample pad 101 is exposed to a suspect substance. This may be accomplished by the swab unit sample pad 101 being swiped across a surface containing the suspect substance or the swab unit pad 101 may be exposed to the suspect substance in other ways such as adding the suspect substance to the swab unit sample pad 101.

The inspection tester 100 comprises an explosives tester body 102 and the removable swab unit 101 adapted to be removably positioned in the explosives tester body 102. The removable swab unit 101 includes a lateral flow membrane 111, an area 112 so that the swab unit can be easily inserted and removed from the explosives tester body 102. The removable swab unit 101 also includes an information area 113 and color reaction indicators 114.

The explosives tester body 102 includes a printable backing card 103 that adds stiffness and infographics. A heat seal pattern 104 adds strength to avoid warping. A section 105 of the explosives tester body 102 provides an area for printed graphics and thumb placement and step numbering. The explosives tester body 102 includes a beveled docking entry portion 106 and a tab 107 for easy docking of the removable swab unit sample pad 101.

The explosives tester body 102 also includes ampoule A 108 and ampoule B 109. In various embodiments, ampoule A 108 and ampoule B 109 are breakable ampoules, breakable glass ampoules, squeezable ampoules, and other types of ampoules. As shown in FIG. 1, ampoule A 108 includes indentations 110 on the chamber which keeps glass pieces from adhering to the walls.

Figure 2:
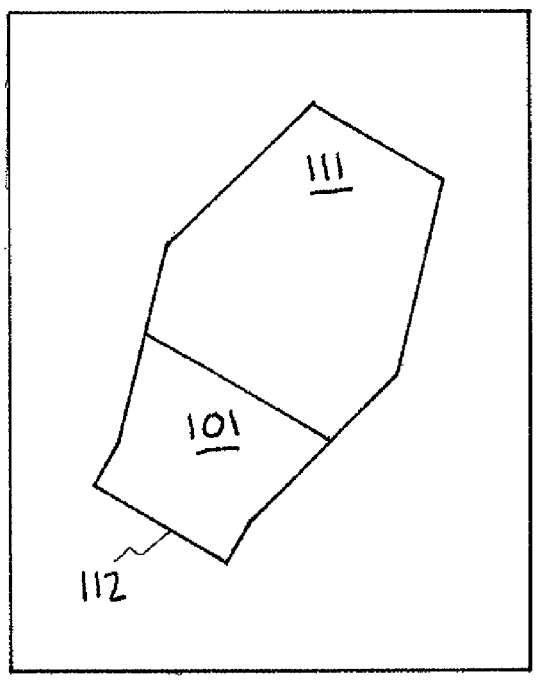
FIG. 2 shows the removable swab unit in greater detail.

The removable swab unit 101 is shown in greater detail in FIG. 2. The tab area 112 is provided so that the swab unit 101 can be easily inserted and removed from the explosives tester body 102. The lateral flow membrane 111 makes up the bulk of the removable swab unit 101. The lateral flow membrane 111 comprises a macroporous membrane that provides migration of fluids from ampoule A 108 and fluids from ampoule B 109. Lateral flow membranes are known for their use in other fields such as blotting techniques, enzyme-linked immunosorbent assay (ELISA) testing, and lateral-flow immunochromatographic tests. The lateral flow membrane 111 is a Porex Lateral-Flo Membrane. The lateral flow membrane 111 comprises polyethylene spheres fused into a Lateral-Flo™ membrane. Applicants experimentally determined that the properties of Porex make it an ideal swipe material for the inspection tester 100. The lateral flow membrane 111 is chemical resistant, withstands heat as high as 130° C., is durable, is inexpensive, can be cut to any size, and concentrates suspect materials along the solvent front making colorimetric detection limits. The lateral flow membrane 111 provides a high surface area swipe for sample collection.

Figure 3:
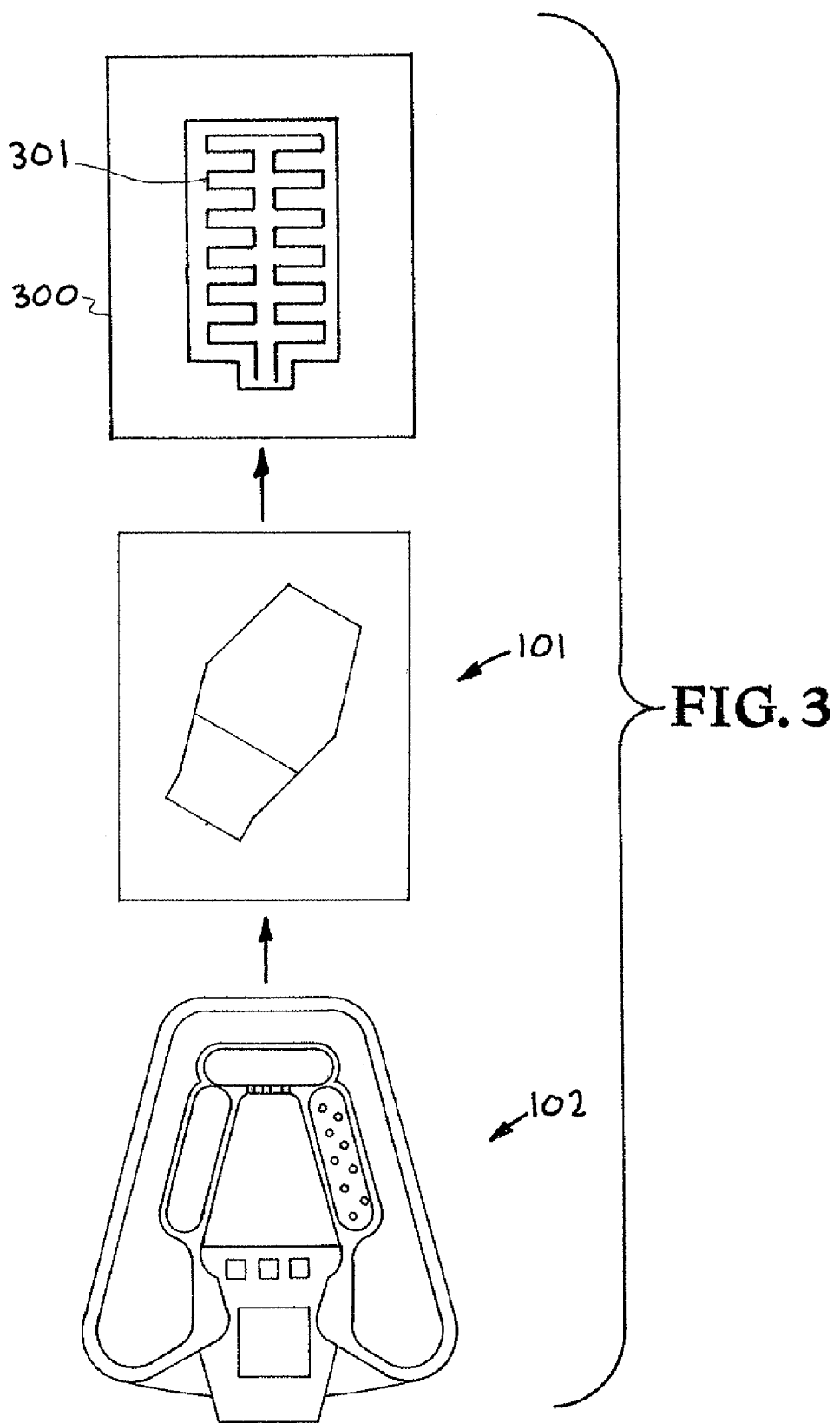
FIG. 3 shows the explosive tester positioned in a portable heating unit.

Referring now to FIG. 3, the removable swab unit 101 of the explosive tester 100 is shown as it would be positioned in a portable heating unit 300. The portable heating unit 300 can be an electrical heater or, alternatively, the portable heating unit 300 can be another type of heating unit such as a chemical heater. The heating element 301 is activated and the removable swab unit 101 will be heated as hereinafter described. The details of the portable heating unit 300 are well known in the art and need not be described here.

Ampoule A 108 and ampoule B 109 provide two reagent activation units. Ampoule A 108 (for reagent A) and ampoule B 109 (for reagent B) are operatively mounted on the explosives tester body 102. The ampoule A 108 containing the first explosives detecting reagent A is positioned to deliver the first explosives detecting reagent A to the lateral flow membrane 111. The Ampoule B 109 containing the second explosives detecting reagent B is positioned to deliver the second explosives detecting reagent B to the lateral flow membrane 111. The reagent A contains Meisenheimer complexes. The reagent B provides a Griess reaction. The Meisenheimer complexes and Griess reaction are well known in the art and need not be described here.

The structural details of embodiment of an inspection tester for explosives constructed in accordance with the present invention having been described the operation of the inspection tester 100 will now be considered. The inspection tester 400 uses a simple and rapid procedure summarized by the following four step operation:

STEP 1) A suspect surface is swiped with the removable swab unit sample pad 101. This may be accomplished by the swab unit sample pad 101 being swiped across a surface containing the suspect substance or the swab unit pad 101 may be exposed to the suspect substance in other ways such as adding the suspect substance to the swab unit sample pad 101. This will cause any explosives residue to be collected and held by the swab unit sample pad 101.

STEP 2) The breakable or squeezable ampoule A 108 is located in a position to deliver the first explosives detecting reagent A to the lateral flow membrane 111. The breakable or squeezable ampoule A 108 is pressed to break or squeeze it thereby dispensing reagent A onto the lateral flow membrane 111. The regent A contacts any explosives residue that has been collected by the swab unit sample pad 101. The lateral flow membrane 111 concentrates suspect materials along the solvent front. If the swab unit sample pad 101 becomes colored, the test is positive for explosives. If no color appears the test for explosives is negative to this point.

STEP 3) If STEP 2 is negative to this point, the inspection tester 100 is positioned in the portable heating unit 300. The heating unit 300 is activated. This causes the swab unit sample pad 101, reagent A, and any explosives residue to become heated. If the swab unit sample pad 101 now becomes colored, the test is positive for explosives. If no color appears the test for explosives is negative to this point.

STEP 4) The breakable or squeezable ampoule B 109 is located in a position to deliver the second explosives detecting reagent B to the lateral flow membrane 111. If STEP 3 is negative to this point, the breakable or squeezable ampoule B 109 is pressed to brake or squeeze it thereby dispensing reagent B onto the lateral flow membrane 111. The regent B contacts any explosives residue that has been collected by the swab unit sample pad 101. The lateral flow membrane 111 concentrates suspect materials along the solvent front. If the swab unit sample pad 101 becomes colored, the test is positive for explosives. If no color appears the test for explosives is negative.

The inspection tester 100 provides a simple, chemical, field spot-test by to provide a rapid screen for the presence of a broad range of explosive residues. The lateral flow membrane 111 is microporous cellulose nitrate membrane that provides migration of the fluids from ampoule A 108 and ampoule B 109. The lateral flow membrane 111 concentrates suspect materials along the solvent front. This concentration makes the explosives tester 100 more sensitive because by concentrating any explosives particles along the solvent front a larger amount of materials in one place. The color that will be produced by the reagents from ampoule A 108 and ampoule B 109 will be easier to see.

The inspection tester 100 is fast, extremely sensitive, low-cost, very easy to implement, and provides a very low rate of false positives. The inspection tester for explosives 100 provides a fast, sensitive, low-cost, very easy to implement system for testing the suspected packages. The inspection tester for explosives 100 is inexpensive and disposable. The inspection tester for explosives 100 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 100 is small enough that a number of them can fit in a pocket or brief case.

Figure 4:
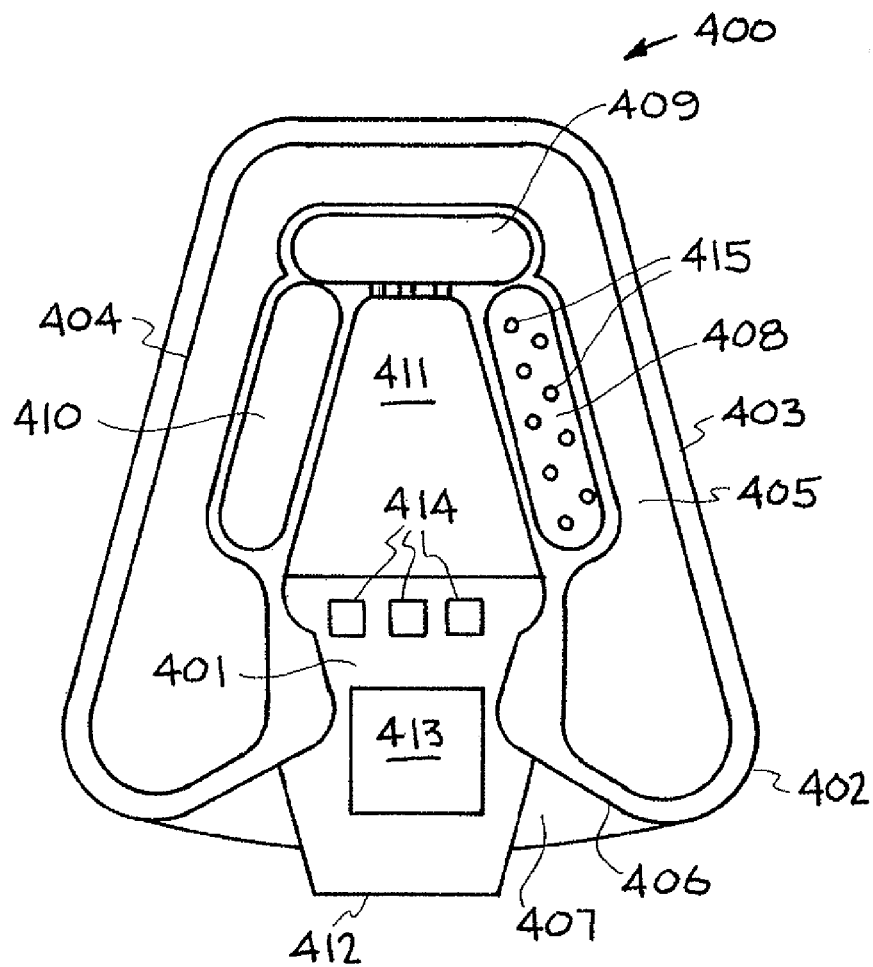
FIG. 4 shows another embodiment of an inspection tester for explosives constructed in accordance with the present invention.

Referring now to FIG. 4 of the drawings, another embodiment of an inspection tester for explosives constructed in accordance with the present invention is illustrated. This embodiment of the present invention is designated generally by the reference numeral 400. A removable swab unit sample pad 401 is exposed to a suspect substance. This may be accomplished by the swab unit sample pad 401 being swiped across a surface containing the suspect substance or the swab unit pad 401 may be exposed to the suspect substance in other ways such as adding the suspect substance to the swab unit sample pad 401.

The inspection tester 400 comprises an explosives tester body 402 and the removable swab unit 401 adapted to be removably positioned in the explosives tester body 402. The removable swab unit 401 includes a lateral flow membrane 411, an area 412 so that the swab unit can be easily inserted and removed from the explosives tester body 402. The removable swab unit 401 also includes and information area 413 and color reaction indicators 414.

The explosives tester body 402 includes a printable backing card 403 that adds stiffness and infographics. A heat seal pattern 404 adds strength to avoid warping. A section 405 of the explosives tester body 402 provides an area for printed graphics and thumb placement and step numbering. The explosives tester body 402 includes a beveled docking entry portion 406 and a tab 407 for easy docking of the removable swab unit sample pad 401.

The explosives tester body 402 also includes three ampoules, #1 ampoule A 408, #2 ampoule B 409, and #3 ampoule C 410. In various embodiments, ampoule A 408, ampoule B 409, and ampoule C 410 are breakable ampoules, breakable glass ampoules, squeezable ampoules, and other types of ampoules. As shown in FIG. 4, ampoule A 408 includes indentations 110 on the chamber which keeps glass pieces from adhering to the walls.

The tab area 412 on the removable swab unit 401 allows the swab unit 401 can be easily inserted and removed from the explosives tester body 402. The lateral flow membrane 411 makes up the bulk of the removable swab unit 401. The lateral flow membrane 411 comprises a microporous cellulose nitrate membrane that provides migration of fluids from ampoule A 408, fluids from ampoule B 409, and fluids from ampoule C 410. The lateral flow membrane 411 is a Porex Lateral-Flo Membrane. The lateral flow membrane 411 comprises polyethylene spheres fused into a Lateral-Flo™ membrane. The lateral flow membrane 411 is chemical resistant, withstands heat as high as 130° C., is durable, is inexpensive, can be cut to any size, and concentrates suspect materials along the solvent front making colorimetric detection limits. The lateral flow membrane 411 provides a high surface area swipe for sample collection.

Ampoule A 408, ampoule B 409, and ampoule C 410 and provide three reagent activation units. Ampoule A 408 (for reagent A), ampoule B 409 (for reagent B) and ampoule C 410 (for reagent C) are operatively mounted on the explosives tester body 402. The ampoule A 408 containing the first explosives detecting reagent A is positioned to deliver the first explosives detecting reagent A to the lateral flow membrane 411. The ampoule B 409 containing the second explosives detecting reagent B is positioned to deliver the second explosives detecting reagent B to the lateral flow membrane 411. The ampoule C 410 containing the third explosives detecting reagent C is positioned to deliver the third explosives detecting reagent C to the lateral flow membrane 411. The reagent A contains Meisenheimer complexes. The reagent B provides a Griess reagent. The reagent C provides a Nesslers reagent. The Meisenheimer complexes, Griess reagent, and Nesslers reagent are well known in the art and need not be described here.

The structural details of embodiment of an inspection tester for explosives constructed in accordance with the present invention having been described the operation of the inspection tester 400 will now be considered. The inspection tester 400 uses a simple and rapid procedure summarized by the following steps:

STEP 1) A suspect surface is swiped with the removable swab unit sample pad 401. This may be accomplished by the swab unit sample pad 401 being swiped across a surface containing the suspect substance or the swab unit pad 401 may be exposed to the suspect substance in other ways such as adding the suspect substance to the swab unit sample pad 401. This will cause any explosives residue to be collected and held by the swab unit sample pad 401.

STEP 2) The breakable or squeezable ampoule A 408 is located in a position to deliver the first explosives detecting reagent A to the lateral flow membrane 411. The breakable or squeezable ampoule A 408 is pressed to break or squeeze it thereby dispensing reagent A onto the lateral flow membrane 411. The regent A contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 3) If STEP 2 is negative to this point, the breakable or squeezable ampoule B 409 is pressed to brake or squeeze it thereby dispensing reagent B onto the lateral flow membrane 411. The breakable or squeezable ampoule B 409 is located in a position to deliver the second explosives detecting reagent B to the lateral flow membrane 411. The regent B contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 4) If STEP 3 is negative to this point, the breakable or squeezable ampoule C 410 is pressed to brake or squeeze it thereby dispensing reagent C onto the lateral flow membrane 411. The breakable or squeezable ampoule C 410 is located in a position to deliver the second explosives detecting reagent C to the lateral flow membrane 411. The regent C contacts any explosives residue that has been collected by the swab unit sample pad 401. The lateral flow membrane 411 concentrates suspect materials along the solvent front. If the swab unit sample pad 401 becomes colored, the test is positive for explosives. If no color appears the test for explosives is negative to this point.

STEP 5) If any of the various STEPS 2, 3, and 4 are negative and greater sensitivity is desired, the inspection tester 400 can be positioned in a heating unit. This causes the swab unit sample pad 401, reagents A, B, and/or C and any explosives residue to become heated. If the swab unit sample pad 401 now becomes colored, the test is positive for explosives. If no color appears the test for explosives is negative.

The inspection tester 400 provides a simple, chemical, field spot-test by to provide a rapid screen for the presence of a broad range of explosive residues. The lateral flow membrane 411 is microporous cellulose nitrate membrane that provides migration of the fluids from ampoule A 408, ampoule B 409, and ampoule C 410. The lateral flow membrane 411 concentrates suspect materials along the solvent front. This concentration makes the explosives tester 400 more sensitive because by concentrating any explosives particles along the solvent front a larger amount of materials in one place. The color that will be produced by the reagents from ampoule A 408, ampoule B 409, and/or ampoule C 410 will be easier to see.

The inspection tester 400 is fast, extremely sensitive, low-cost, very easy to implement, and provides a very low rate of false positives. The inspection tester for explosives 400 provides a fast, sensitive, low-cost, very easy to implement system for testing the suspected packages. The inspection tester for explosives 400 is inexpensive and disposable. The inspection tester for explosives 400 has detection limits between 0.1 to 100 nanograms, depending on the type of explosives present. A large number of common military and industrial explosives can be easily detected such as HMX, RDX, NG, TATB, Tetryl, PETN, TNT, DNT, TNB, DNB and NC. The inspection tester 400 is small enough that a number of them can fit in a pocket or brief case.

While the invention may be susceptible to various modifications and alternative formis, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An inspection tester method for testing a suspect surface for explosives wherein the explosives are explosives particles, consisting of the steps of:
   providing an explosives detecting lateral flow membrane with polyethylene spheres fused into said membrane for collecting the explosives particles,
   providing a lateral flow membrane swab unit containing said explosives detecting lateral flow membrane with polyethylene spheres fused into said membrane for collecting the explosives particles,
   providing a first explosives detecting reagent;
   providing a second explosives detecting reagent;
   swiping the suspect surface with said lateral flow membrane swab unit containing said explosives detecting lateral flow membrane with polyethylene spheres fused into said membrane for collecting the explosives particles wherein the explosives particles are picked up by said lateral flow membrane swab unit containing said explosives detecting lateral flow membrane with polyethylene spheres fused into said membrane for collecting the explosives particles,
   delivering said first explosives detecting reagent to said lateral flow membrane swab unit containing said explosives detecting lateral flow membrane with polyethylene spheres fused into said membrane for collecting the explosives particles and the explosives particles picked up in said step of swiping the suspect surface and producing a solvent front concentrating the explosives particles along said solvent front and concentrating the explosives particles in one place, wherein if said lateral flow membrane swab unit containing said explosives detecting lateral flow membrane with polyethylene spheres fused into said membrane for collecting the explosives particles becomes colored the test is positive for explosives and if no color appears the test for explosives is negative to this point; and
   delivering said second explosives detecting reagent to said lateral flow membrane swab unit containing said explosives detecting lateral flow membrane with polyethylene spheres fused into said membrane for collecting the explosives particles, wherein if said lateral flow membrane swab unit containing said explosives detecting lateral flow membrane with polyethylene spheres fused into said membrane for collecting the explosives particles becomes colored the test is positive for explosives and if no color appears the test for explosives is negative.

\* \* \* \* \*